United States Patent
McCarthy

(10) Patent No.: US 11,077,317 B2
(45) Date of Patent: Aug. 3, 2021

(54) INTRAVENOUS RADIATION TREATMENT METHOD

(71) Applicant: Warren Z McCarthy, Salt Lake City, UT (US)

(72) Inventor: Warren Z McCarthy, Salt Lake City, UT (US)

( * ) Notice: Subject to any disclaimer, the term of this patent is extended or adjusted under 35 U.S.C. 154(b) by 362 days.

(21) Appl. No.: 16/182,585

(22) Filed: Jan. 23, 2019

(65) Prior Publication Data

US 2019/0160299 A1    May 30, 2019

(51) Int. Cl.
*A61N 5/06* (2006.01)
*A61B 34/00* (2016.01)
*A61K 41/00* (2020.01)
*A61K 49/18* (2006.01)

(52) U.S. Cl.
CPC ............ *A61N 5/0601* (2013.01); *A61B 34/73* (2016.02); *A61K 41/0057* (2013.01); *A61K 49/1824* (2013.01); *A61N 5/062* (2013.01); *A61B 2034/733* (2016.02); *A61N 2005/0602* (2013.01); *A61N 2005/0628* (2013.01); *A61N 2005/0651* (2013.01); *A61N 2005/0659* (2013.01); *A61N 2005/0661* (2013.01); *A61N 2005/0663* (2013.01)

(58) Field of Classification Search
None
See application file for complete search history.

(56) References Cited

U.S. PATENT DOCUMENTS

| | | | | |
|---|---|---|---|---|
| 5,571,152 A | * | 11/1996 | Chen | A61N 5/0601 604/21 |
| 2005/0090732 A1 | * | 4/2005 | Ivkov | A61N 2/002 600/411 |
| 2006/0147371 A1 | * | 7/2006 | Tuszynski | A61K 45/06 424/1.11 |
| 2012/0053512 A1 | | 3/2012 | Muse | |
| 2012/0149981 A1 | * | 6/2012 | Khait | A61B 1/00158 600/109 |
| 2014/0200489 A1 | * | 7/2014 | Behar | A61N 7/00 601/3 |
| 2018/0214707 A1 | * | 8/2018 | Li | A61K 41/00 |
| 2020/0246179 A1 | * | 8/2020 | Peyman | A61K 9/127 |

FOREIGN PATENT DOCUMENTS

| | | | | |
|---|---|---|---|---|
| CN | 101175437 A | * | 5/2008 | ............ A61N 5/062 |
| CN | 101374379 A | * | 2/2009 | ............ A61N 5/062 |
| WO | WO-2007110259 A1 | * | 10/2007 | ........ A61B 1/00158 |
| WO | WO-2008110545 A1 | * | 9/2008 | ............ A61B 34/73 |

* cited by examiner

*Primary Examiner* — Amy R Weisberg

(57) ABSTRACT

A method has been invented for intravenously inserting a tumor reduction radiation emitter into the body of a patient suffering from a cancerous tumor. The emitter is very small, yet detectable by medical imaging techniques and guidable by use of magnetism. The emitter is guided through the body by use of a magnet until it is adjacent or in in the tumor itself. The emitter can be oriented in various desired directions by the magnet. The emitter is then wirelessly powered by electrical induction, causing the radiation of a desired wavelength to be directed to tumor cells, causing tumor reduction.

17 Claims, 4 Drawing Sheets

INTRAVENOUS RADIATION TREATMENT METHOD

BACKGROUND

In the prior art, there has been research performed related to radiation and photonic treatment of malignant tumors. For example, in the prior art methods, a dye sensitive to light of a pre-determined wavelength is injected into the tumor. Then from outside of the body radiation of a visible wavelength is applied which is absorbed by the dye, heating the tumor cells and killing them.

SUMMARY OF THE INVENTION

A method has been invented for intravenously inserting a tumor reduction radiation emitter with radiation emission module into the body of a patient suffering from a cancerous tumor. The tumor reduction radiation emitter is very small, yet detectable by medical imaging techniques and guidable by use of magnetism. The tumor reduction radiation emitter is guided through arterial or venous passages until it is in or adjacent to the tumor itself. The tumor reduction radiation emitter can be oriented in various desired directions by magnetism. The tumor reduction radiation emitter is then wirelessly powered by electrical induction, causing the radiation emission module to emit radiation of a desired wavelength, which may or may not include visible light. As the tumor reduction radiation emitter is within venous or arterial pathways of the tumor or adjacent to the tumor, the tumor tissue is exposed to the emitted radiation, causing the tumor tissue to suffer necrosis and causing the tumor to be reduced or entirely eliminated. Optionally, a light-absorbing material can be introduced to the tumor prior to treatment in order to cause the radiation emitted to be more efficient or more effective, or to otherwise distinguish between tumor tissue and normal tissue. Alternatively, the wavelength of radiation emitted can be tuned to the wavelength of radiation which the tumor cells absorb. Or the wavelength of radiation emitted ca be tuned to the wavelength of radiation absorbed by a material which is in or near tumor cells. The tumor reduction radiation emitter can be removed from the body or it can be allowed to remain for future treatments.

DETAILED DESCRIPTION OF THE INVENTION

As an introductory matter, consideration must be given to powering a small intravenous tumor reduction radiation emitter located within a human body without the use of an internal battery and without the use of wires extending to a power source located outside of the body, in order to achieve the smallest intravenous tumor reduction photonic emitter possible. Providing wireless power by electrical induction operates by principles similar to those used in electric motors. When an alternating electrical current is applied to a transformer, an alternating magnetic field is created. When a secondary transformer is located within the magnetic field, an electric current will be induced in the secondary transformer. Resistance within the secondary transformer causes it to heat up. In an example simple induction heating assembly, a copper coil is obtained, and a conductive (often ferrous) object is placed inside of or adjacent to the coil. AC current is run through the coil and this creates an alternating magnetic field. The alternating magnetic field induces eddy currents within the conductive object. Current induced within the conductive object can be used to power a light emitting diode, laser chip, lamp or other radiation source which is part of the intravenous tumor reduction radiation emitter. In this way, an electrical induction-powered tumor reduction radiation emitter is provided. The field of electrical induction has been well-researched and documented and it is not necessary to replicate that knowledge base here.

Consideration must also be given to locating an electrical induction-powered tumor reduction radiation emitter within or adjacent to tumor tissue so that it treats the tumor intended to be reduced with minimal effects on healthy tissue. Accessing a vein, artery or other passageway within the human body adjacent a tumor may be difficult without surgery. Therefore the invention provides for placement of an electrical induction-powered tumor reduction radiation emitter within a vein, artery or other passageway of a human patient, and then using a magnet to draw such electrical induction-powered tumor reduction radiation emitter along such passageway of a human patient until it is within or adjacent to a tumor. When in such location, the electrical induction-powered tumor reduction radiation emitter can be wireless powered by electrical induction so that emitted radiation can serve to reduce the tumor.

Figure 1:
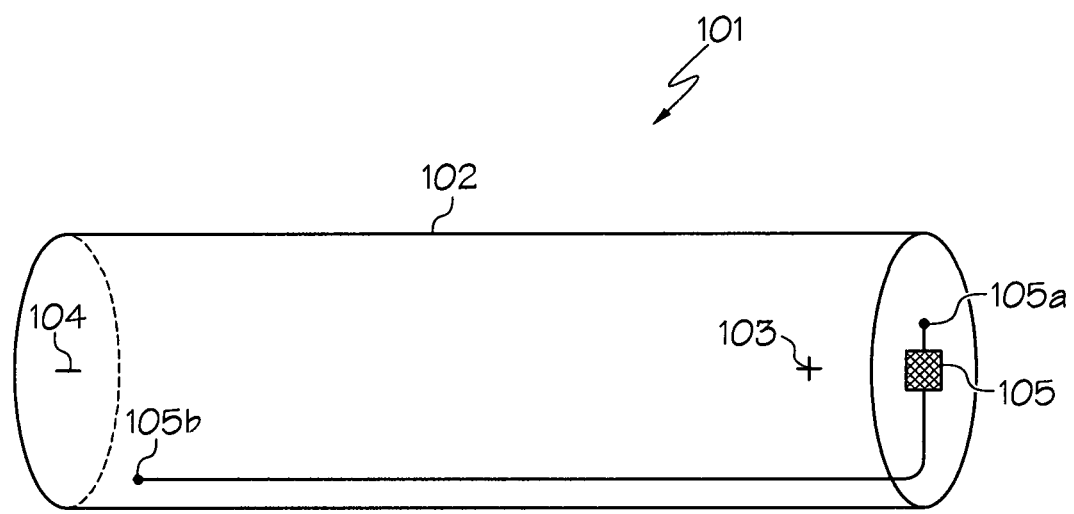
FIG. 1 depicts an intravenous tumor reduction radiation emitter.

FIG. 1 depicts an electrical induction-powered intravenous tumor reduction radiation emitter 101. Although it is referred to in this document as an intravenous tumor reduction radiation emitter, it can be used intravenously, within arteries, within the digestive tract, or within other passageways or tissues of the human body. The intravenous tumor reduction radiation emitter 101 has an elongate conductive body 102 with a positive pole 103 and a negative pole 104. Attached to the elongate conductive body is a radiation emission module 105 which is in electrically conductive contact through leads 105a and 105b to the poles 103 and 104. The radiation emission module 105 can be attached to the elongate body 102 by use of adhesive, glue, epoxy, welding, mechanical fixation or otherwise. The radiation emission module 105 can be an LED, a semiconductor laser, a lamp, or any other device capable of emitting radiation of a wavelength and intensity sufficient to directly or indirectly cause necrosis of tumor tissue, thereby achieving tumor reduction. Alternatively, the radiation emitted can be of a wavelength and intensity that causes the affected tumor tissue to uptake a molecule which brings about reduction of the tumor. The molecule could be a medicine, a pharmaceutical, a toxin, a protein, a hormone or otherwise. Preferably, the size of the electrical induction-powered intravenous tumor reduction radiation emitter will be sufficiently small to allow it to be inserted into a venous or arterial passageway of a human body. The electrical induction-powered intravenous tumor reduction radiation emitter can preferably be moved and re-oriented within such passageway by use of a magnet.

Figure 2:
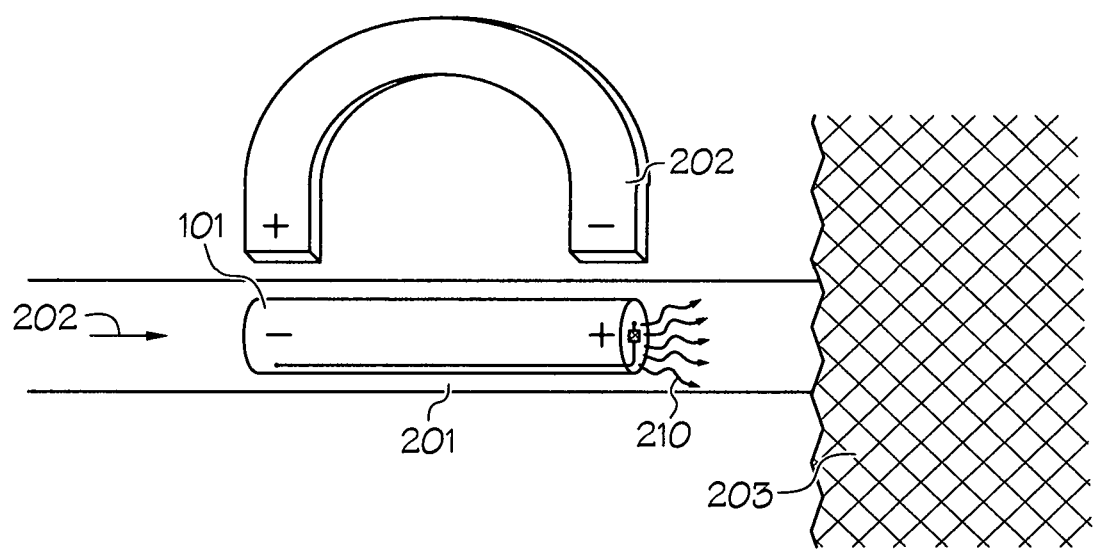
FIG. 2 depicts an intravenous tumor reduction radiation emitter within a venous or arterial passageway of a human body being directed toward the location of a tumor.

FIG. 2 depicts an intravenous tumor reduction radiation emitter 101 located within a venous passageway 201 of a human patient. A magnet 202 external to the patient can be used to cause the intravenous tumor reduction radiation emitter 101 to travel within the venous passageway 201 in the direction of arrow 202 toward a tumor 203. The external magnet 202 can also be used to orient the intravenous tumor reduction radiation emitter 101 in a direction such that radiation 210 from its radiation emission module 105 can be caused to travel in a direction where undesirable tumor tissue is located.

Figure 3:
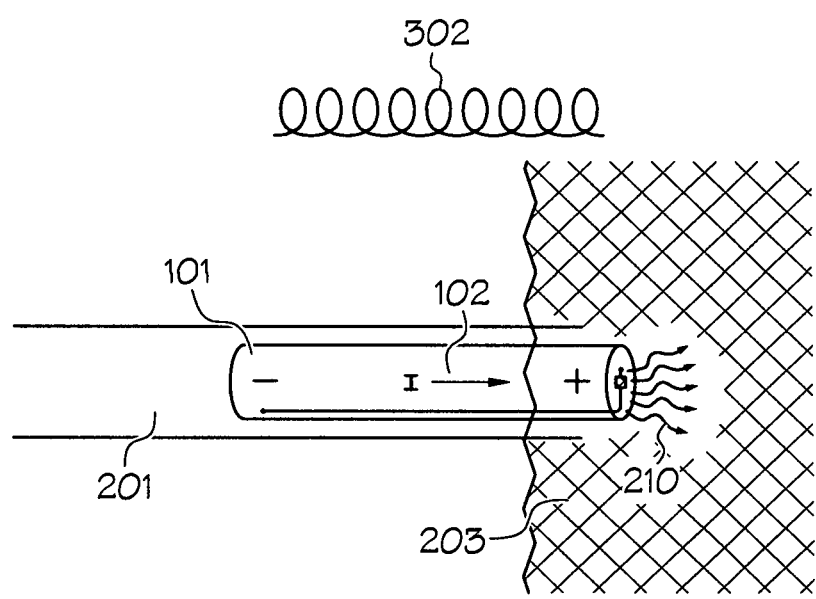
FIG. 3 depicts an intravenous tumor reduction radiation emitter within a venous or arterial passageway of a tumor, and being caused to emit photonic radiation by powering the tumor reduction radiation emitter with electrical induction.

FIG. 3 depicts an intravenous tumor reduction radiation emitter 101 within a venous or arterial passageway 201 of a tumor 203, and being caused to emit radiation 310 by powering the tumor reduction radiation emitter 101 through electrical induction. Electrical induction is brought about by a rapidly changing magnetic field from coil 302 located outside of the patient. The coil can be wrapped around the patient or adjacent to the patient, but is external to the patient. Electrical induction creates current I within the elongate conductive body 102 of the intravenous tumor reduction radiation emitter 101 to power the radiation emission module 105. Radiation 303 from the radiation emission module 105 travels to tumor 203, causing necrosis of tumor tissue, thereby reducing or eliminating the tumor 203. A magnet can be used to move the intravenous tumor reduction radiation emitter within the tumor and to re-orient the intravenous tumor reduction radiation emitter 101 within the tumor to direct radiation in a desired direction. Location and orientation of the intravenous tumor reduction radiation emitter within a human body can be monitored through known medical imaging techniques.

The wavelength of photonic radiation used in this method can be narrow band or wide band, depending on the application. The photonic radiation can be collimated or otherwise, as desired. The wavelength of the photonic radiation can be any wavelength found to cause necrosis of tumor tissues varies, depending on the type of tissue and whether any photon-absorbing material (such as dye or other material) is introduced to the tumor. If the photonic radiation device is a light-emitting diode, then the wavelength of photonic radiation used for tumor reduction may be 240-360 nm, 395-530 nm, 565-645 nm, 660-900 nm, or otherwise. If the photonic radiation device is a laser, then the wavelength of photonic radiation used for tumor reduction may be 110 nm to 20,000 nm, or otherwise. It is expected that in most instances, light used to reduce human tumors will be in the range of 280 nm to 1080 nm. As new sources of photonic radiation are invented, some of those new devices may be useful in the present invention. Any photonic radiation which causes sufficient necrosis of tumor tissue to result in tumor reduction can be useful in the invention. Some investigation may be necessary to match the wavelength of photonic radiation to tumor type for best results.

Figure 4:
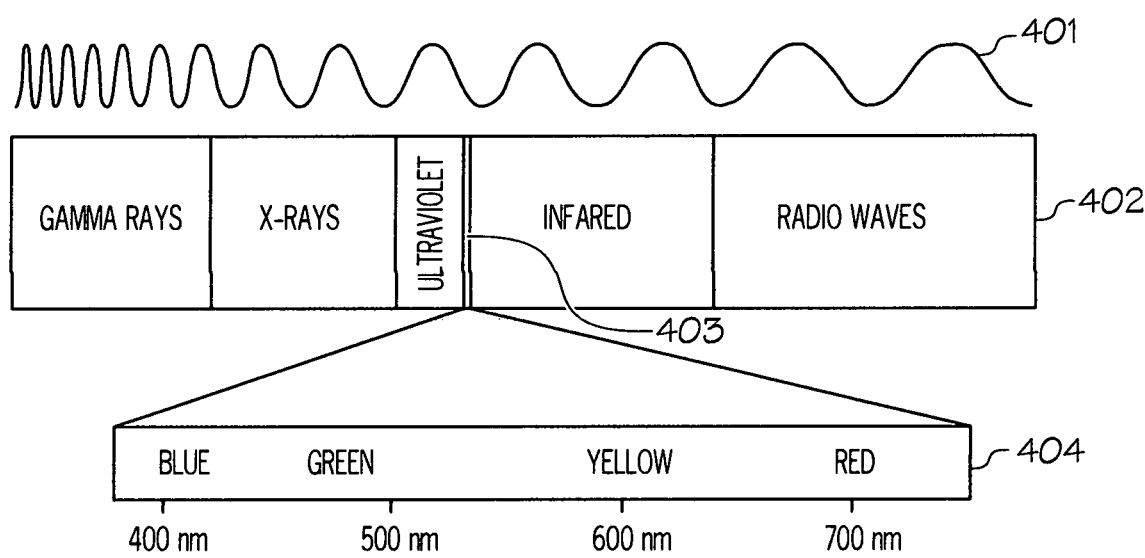
FIG. 4 depicts example wavelengths of radiation which may be chosen to be emitted by an intravenous tumor reduction radiation emitter.

FIG. 4 depicts example wavelengths of radiation that can be used in the invented method. Wavelengths of radiation 401 are represented by a sine wave, going from short to long wavelengths. This corresponds to a wavelength chart 402 which shows gamma rays at 0.001 nm, x-rays at 0.01 nm to 10 nm, then visible light in a narrow band 403 from about 375 nm to 750 nm, followed by infrared radiation at about 1000 nm to 0.01 cm, followed by radio waves at about 1 cm to 100 m or more. The narrow band of visible light 403 can be expanded into a spectrum 404 showing blue, green, yellow and red light. The invention can use any of these wavelengths of radiation and others. The radiation used to reduce a tumor can be visible light, also known as photonic radiation, or otherwise.

In the invention, the wavelength of radiation emitted by the radiation emission module can be tuned to the wavelength absorbed by the tissue of the tumor which is desired to be reduced. Different types of cancerous tumors will absorb different wavelengths of radiation. Tuning the wavelength of radiation emitted can improve efficiency and efficacy of treatment.

Alternatively, if a radiation-absorbing material such as a dye is introduced to the tumor prior to treatment, then the wavelength of radiation emitted by the radiation emission module can be tuned to the wavelength absorbed by the radiation-absorbing material.

It is also possible to introduce nanoparticles of a metal, a ceramic, a polymer, or other solid material to the tumor and then to expose the tumor to radiation so that the nanoparticles absorb the radiation, heat up, and cause necrosis of the tumor tissue.

It is known that cancerous tumors burn glucose at an elevated rate compared to healthy cells. Therefore, an embodiment of the invention includes additional steps to take advantage of that fact. First, the patient either fasts or substantially reduces carbohydrate intake for 3 or 4 days before treatment, causing the patient's blood sugar to drop and causing the patient to enter a state of ketosis. In this state, the cancer cells are starving because they cannot burn ketones. Next, glucose and insulin are injected into the blood supply for the cancerous tumor. This will cause the cells of the cancerous tumor to rapidly uptake huge amounts of glucose, while the rest of the patient's body is in ketosis. Then an intravenous tumor reduction radiation emitter is used to emit radiation in the direction of tumor cells of a wavelength tuned to glucose molecules. The radiation causes the glucose to increase in temperature and die off. A variation of this embodiment would pair a tag-along molecule with glucose so that when the tumor cells uptake glucose, the tag-along molecule can be exposed to radiation tuned to it, heating that molecule and again heating cancer cells and causing necrosis. Another variation of this embodiment tunes the radiation emitted to a unique protein that is found in or on cancer cells but not found in large quantities in healthy tissue. With that protein targeted, the radiation emitted can heat the protein and kill cancer cells.

The invention may be implemented with one ore more of the steps above omitted, or with new steps added, or with any variation of the structures, materials and processes described in the foregoing pages.

The invention claimed is:

1. A method for reducing a malignant tumor within the body of a human patient comprising the stops of:
   placing an electrical induction-powered intravenous tumor reduction radiation emitter within a venous passageway of the human patient,
   said intravenous tumor reduction radiation emitter including
   an elongate conductive body with a positive pole and a negative pole,
   a radiation emission module affixed to said elongate conductive body,
   said radiation emission module being in electrically conductive contact with said poles,
   said radiation emission module being capable of emitting radiation of a wavelength and intensity sufficient to cause necrosis of tumor tissue in order to achieve tumor reduction, using a magnet to guide said intravenous tumor reduction radiation emitter along said venous passageway to the location of a tumor in the body of said patient, using a magnet to orient said intravenous tumor reduction radiation emitter so that radiation which it emits is directed toward tissue of said tumor, locating said human patient and an electrical induction coil in proximity with each other, powering said induction coil to induce an electrical current in said elongate conductive body of said intravenous tumor reduction radiation emitter, allowing said electrical current to power said radiation emission module to cause it to emit radiation within said patient, and causing said emitted radiation to affect tumor tissue, thereby causing necrosis of said tumor tissue and reducing said tumor.

2. A method as recited in claim 1 further comprising the step of monitoring the location of said intravenous tumor reduction photonic emitter within said patient's body via medical imaging.

3. A method as recited in claim 1 further comprising the step of tuning the wavelength of radiation emitted by said radiation emission module to a wavelength that is absorbable by the tumor to be reduced.

4. A method as recited in claim 1 further comprising the step of tuning the wavelength of radiation emitted by said radiation emission module to a wavelength that is absorbable by a protein located on cells of the tumor to be reduced.

5. A method as recited in claim 1 further comprising the step of tuning the wavelength of radiation emitted by said radiation emission module to a wavelength that is absorbable by a protein located on cells of the tumor to be reduced.

6. A method as recited in claim 1 further comprising the step of introducing a radiation-absorbing material into blood supply of said tumor.

7. A method as recited in claim 6 further comprising the step of tuning the wavelength of radiation emitted by said radiation emission module to a wavelength that is absorbable by said radiation-absorbing material to enhance transmission of radiation energy to the tumor to be reduced.

8. A method as recited in claim 7 wherein said radiation-absorbing material is a dye.

9. A method as recited in claim 7 wherein said radiation-absorbing material is a metal nanoparticle.

10. A method as recited in claim 7 wherein said radiation-absorbing material is a polymer.

11. A method as recited in claim 1 wherein said radiation emission module is a semiconductor laser.

12. A method as recited in claim 1 wherein said radiation emission module is a light emitting diode.

13. A method as recited in claim 1 wherein said emitted radiation emission module emits a wavelength in the range of about 280 nm to 1080 nm.

14. A method for reducing a malignant tumor within the body of a human patient comprising the stops of:

depriving the patient of substantial carbohydrates for a period of time to cause the patient's blood sugar to drop, thereby causing the patient to go into a state of ketosis so that the patient's healthy cells burn ketones, introducing glucose and insulin to the blood supply for the tumor to be reduced, placing an electrical induction-powered intravenous tumor reduction radiation emitter within a venous passageway of the human patient, said intravenous tumor reduction radiation emitter including an elongate conductive body with a positive pole and a negative pole, a radiation emission module affixed to said elongate conductive body, said radiation emission module being in electrically conductive contact with said poles, said radiation emission module being capable of emitting radiation of a wavelength and intensity sufficient to cause necrosis of tumor tissue in order to achieve tumor reduction, using a magnet to guide said intravenous tumor reduction radiation emitter along said venous passageway to the location of a tumor in the body of said patient, using a magnet to orient said intravenous tumor reduction radiation emitter so that radiation which it emits is directed toward tissue of said tumor, locating said human patient and an electrical induction coil in proximity with each other, powering said induction coil to induce an electrical current in said elongate conductive body of said intravenous tumor reduction radiation emitter, allowing said electrical current to power said radiation emission module to cause it to emit radiation within said patient, and causing said emitted radiation to affect tumor tissue, thereby causing necrosis of said tumor tissue and reducing said tumor.

15. A method as recited in claim 14 further comprising the step of targeting the wavelength of said radiation to a wavelength absorbed by glucose.

16. A method as recited in claim 14 further comprising the steps of

Identifying a protein located in tumor tissue which is not generally present in healthy tissue, targeting the wavelength of said radiation to a wavelength absorbed by said protein.

17. A method as recited in claim 14 further comprising the steps of introducing a tag-along molecule to said glucose, and targeting the wavelength of said radiation to a wavelength absorbed by said tag-along molecule.

* * * * *